US011299525B2

(12) United States Patent
Li et al.

(10) Patent No.: US 11,299,525 B2
(45) Date of Patent: Apr. 12, 2022

(54) CHIMERIC ANTIGEN RECEPTOR-MODIFIED IMMUNE EFFECTOR CELL CARRYING PD-L1 BLOCKING AGENT

(71) Applicant: CRAGE medical Co., Limited, Mongkok Kowloon (HK)

(72) Inventors: Zonghai Li, Shanghai (CN); Zeyan Pan, Shanghai (CN); Zhimin Shi, Shanghai (CN); Bo Song, Shanghai (CN); Peng Wang, Shanghai (CN)

(73) Assignee: CRAGE Medical Co., Limited, Mongkok Kowloon (HK)

( * ) Notice: Subject to any disclaimer, the term of this patent is extended or adjusted under 35 U.S.C. 154(b) by 132 days.

(21) Appl. No.: 15/775,769

(22) PCT Filed: Oct. 31, 2016

(86) PCT No.: PCT/CN2016/103941
§ 371 (c)(1),
(2) Date: May 11, 2018

(87) PCT Pub. No.: WO2017/080377
PCT Pub. Date: May 18, 2017

(65) Prior Publication Data
US 2018/0327470 A1 Nov. 15, 2018

(30) Foreign Application Priority Data
Nov. 13, 2015 (CN) .......................... 201510779876.5

(51) Int. Cl.
| | | |
|---|---|---|
| *A61K 35/17* | (2015.01) | |
| *A61P 35/00* | (2006.01) | |
| *C12N 5/10* | (2006.01) | |
| *C12N 15/62* | (2006.01) | |
| *C12N 15/63* | (2006.01) | |
| *C07K 14/47* | (2006.01) | |
| *A61K 39/17* | (2006.01) | |
| *C12N 5/0783* | (2010.01) | |

(52) U.S. Cl.
CPC .......... *C07K 14/4747* (2013.01); *A61K 35/17* (2013.01); *A61K 39/17* (2013.01); *A61P 35/00* (2018.01); *C12N 5/0638* (2013.01); *C12N 5/10* (2013.01); *C12N 15/62* (2013.01); *C12N 15/63* (2013.01)

(58) Field of Classification Search
CPC .... C07K 14/4747; C12N 5/10; C12N 5/0638; A61P 35/00; A61K 35/17
USPC .................................................... 424/154.1
See application file for complete search history.

(56) References Cited

U.S. PATENT DOCUMENTS

| | | | |
|---|---|---|---|
| 2014/0105934 | A1 | 4/2014 | Lan et al. |
| 2014/0219975 | A1 | 8/2014 | June et al. |
| 2018/0327470 | A1 | 11/2018 | Li et al. |

FOREIGN PATENT DOCUMENTS

| | | | | |
|---|---|---|---|---|
| CN | 101602808 | A | 12/2009 | |
| CN | 103442768 | A | 12/2013 | |
| CN | 103492406 | A | 1/2014 | |
| CN | 105331585 | A | 2/2016 | |
| CN | 106349389 | A | 1/2017 | |
| JP | 2014-524234 | A | 9/2014 | |
| WO | WO 2012/079000 | A1 | 6/2012 | |
| WO | WO 2012/099973 | A2 | 7/2012 | |
| WO | WO 2014/130657 | A1 | 8/2014 | |
| WO | WO 2014/134165 | A1 | 9/2014 | |
| WO | WO 2014/153270 | A1 | 9/2014 | |
| WO | WO 2016/203048 | | * 12/2016 | ........... C07K 14/435 |

OTHER PUBLICATIONS

Supplementary European Search Report dated May 9, 2019 in connection with EP Patent Application No. 16863554.
[No. Author Listed] "Human PD-1 gene fragment, SEQ ID 23"; XP002793532; EBI Accession No. GSN:BBF24805; Jun. 5, 2014, 1 page.
He et al., Blocking programmed death-1 ligand-PD-1 interactions by local gene therapy results in enhancement of antitumor effect of secondary lymphoid tissue chemokine. J Immunol. Oct. 15, 2004;173(8):4919-28.
John et al., Anti-PD-1 antibody therapy potently enhances the eradication of established tumors by gene-modified T cells. Clin Cancer Res. Oct. 15, 2013;19(20):5636-46. doi: 10.1158/1078-0432. CCR-13-0458. Epub Jul. 19, 2013.
Moon et al., Multifactorial T-cell hypofunction that is reversible can limit the efficacy of chimeric antigen receptor-transduced human T cells in solid tumors. Clin Cancer Res. Aug. 15, 2014;20(16):4262-73. doi: 10.1158/1078-0432.CCR-13-2627. Epub Jun. 11, 2014.
Sampson et al., EGFRvIII mCAR-modified T-cell therapy cures mice with established intracerebral glioma and generates host immunity against tumor-antigen loss. Clin Cancer Res. Feb. 15, 2014;20(4):972-84. doi:10.1158/1078-0432.CCR-13-0709. Epub Dec. 18, 2013.
International Search Report and Written Opinion dated Jan. 25, 2017 in connection with Application No. PCT/CN2016/103941.
International Preliminary Report on Patentability dated May 15, 2018 in connection with Application No. PCT/CN2016/103941.
Cao et al., Development of Chimeric Antigen Receptor-Modified T Cells for Treatment of Malignances. J Lanzhou Univ. Med. Sci. Feb. 8, 2015;41(1):1-8.

(Continued)

*Primary Examiner* — Yan Xiao
(74) *Attorney, Agent, or Firm* — Wolf, Greenfield & Sacks, P.C.

(57) ABSTRACT

Provided is a chimeric antigen receptor-modified immune effector cell carrying a procedural death ligand 1 (PD-L1) blocking agent. Also provided is a method for secreting and expressing a PD-L1 blocking agent using the immune effector cell as a carrier to improve the anti-tumour effect of the chimeric antigen receptor-modified immune effector cell.

11 Claims, 4 Drawing Sheets
Specification includes a Sequence Listing.

(56) References Cited

OTHER PUBLICATIONS

Strauss et al., Cancer gene therapy with T cell receptors and chimeric antigen receptors. Curr Opin Pharmacol. Oct. 2015;24:113-8. doi:10.1016/j.coph.2015.08.006. Epub Sep. 4, 2015. Review.
Supplementary European Search Report dated Sep. 5, 2019 in connection with EP Patent Application No. 16863554.
Hartmann et al., Clinical Development of CAR T Cells-Challenges and Opportunities in Translating Innovative Treatment Concepts. EMBO Mol Med. Sep. 2017;9(9):1183-1197. doi: 10.15252/emmm.201607485.
John et al., Blockade of PD-1 immunosuppression boosts CAR T-cell therapy. OncoImmunology. Oct. 2013; 2(10): e26286.
Shi et al., Chimeric Antigen Receptor for Adoptive Immunotherapy of Cancer: Latest Research and Future Prospects. Mol Cancer. Sep. 21, 2014;13:219. doi: 10.1186/1476-4598-13-219.
Xiao et al., Soluble PD-1 Facilitates 4-1BBL-triggered Antitumor Immunity Against Murine H22 Hepatocarcinoma in Vivo. Clin Cancer Res. Mar. 15, 2007;13(6):1823-30. doi: 10.1158/1078-0432.CCR-06-2154. Epub Feb. 26, 2007.
Zhang, CAR T-cell Therapy: Opportunities and Challenges. Immunotherapy. 2016;8(3):245-7. doi: 10.2217/imt.15.129. Epub Feb. 9, 2016.

\* cited by examiner

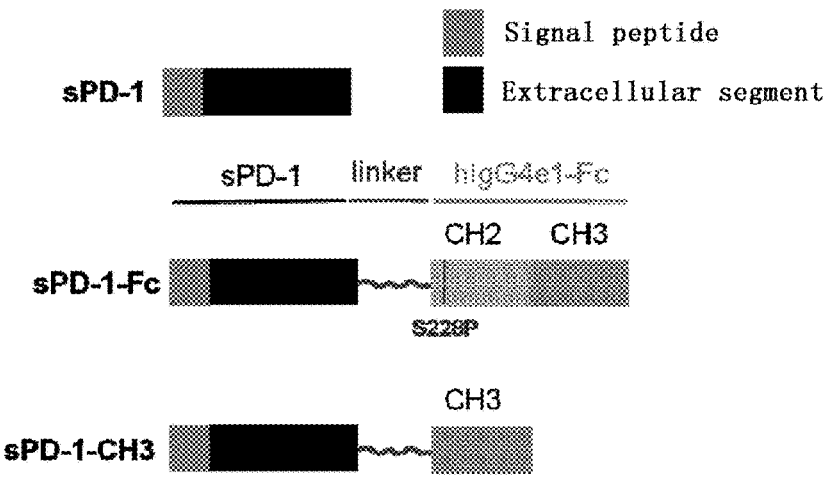
FIG. 1
FIG. 2
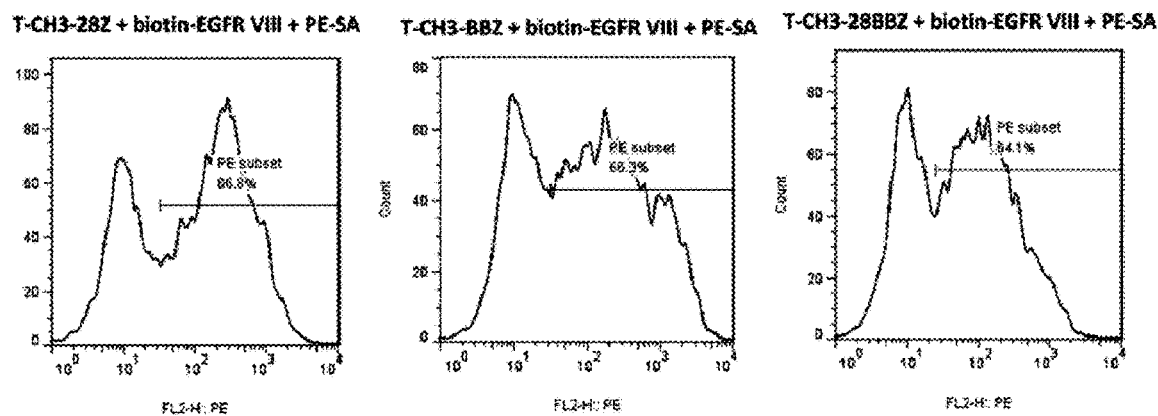

SEQUENCE LISTING

```
<160> NUMBER OF SEQ ID NOS: 16

<210> SEQ ID NO 1
<211> LENGTH: 60
<212> TYPE: DNA
<213> ORGANISM: Artificial sequence
<220> FEATURE:
```

<221> NAME/KEY: misc_feature
<223> OTHER INFORMATION: PD-1 signal peptide sequence

<400> SEQUENCE: 1

```
atgcagatcc cacaggcgcc ctggccagtc gtctgggcgg tgctacaact gggctggcgg    60
```

<210> SEQ ID NO 2
<211> LENGTH: 450
<212> TYPE: DNA
<213> ORGANISM: Artificial sequence
<220> FEATURE:
<221> NAME/KEY: misc_feature
<223> OTHER INFORMATION: PD-1 extracellular segment sequence

<400> SEQUENCE: 2

```
ccaggatggt tcttagactc cccagacagg ccctggaacc cccccacctt ctccccagcc    60
ctgctcgtgg tgaccgaagg ggacaacgcc accttcacct gcagcttctc caacacatcg   120
gagagcttcg tgctaaactg gtaccgcatg agccccagca accagacgga caagctggcc   180
gccttccccg aggaccgcag ccagcccggc caggactgcc gcttccgtgt cacacaactg   240
cccaacgggc gtgacttcca catgagcgtg gtcagggccc ggcgcaatga cagcggcacc   300
tacctctgtg gggccatctc cctggccccc aaggcgcaga tcaaagagag cctgcgggca   360
gagctcaggg tgacagagag aagggcagaa gtgcccacag cccaccccag cccctcaccc   420
aggccagccg gccagttcca aaccctggtg                                    450
```

<210> SEQ ID NO 3
<211> LENGTH: 321
<212> TYPE: DNA
<213> ORGANISM: Artificial sequence
<220> FEATURE:
<221> NAME/KEY: misc_feature
<223> OTHER INFORMATION: DNA sequence of CH3 domain

<400> SEQUENCE: 3

```
gggcagcccc gagagccaca ggtgtacacc ctgcccccat cccaggagga gatgaccaag    60
aaccaggtca gcctgacctg cctggtcaaa ggcttctacc ccagcgacat cgccgtggag   120
tgggagagca atgggcagcc ggagaacaac tacaagacca cgcctcccgt gctggactcc   180
gacggctcct tcttcctcta cagcaggcta accgtggaca agagcaggtg caggaggggg   240
aatgtcttct catgctccgt gatgcatgag gctctgcaca accactacac acagaagagc   300
ctctcccctgt ctccgggtaa a                                            321
```

<210> SEQ ID NO 4
<211> LENGTH: 672
<212> TYPE: DNA
<213> ORGANISM: Artificial sequence
<220> FEATURE:
<221> NAME/KEY: misc_feature
<223> OTHER INFORMATION: DNA sequence of hIgG4e1-Fc domain

<400> SEQUENCE: 4

```
cccccatgcc caccatgccc agcacctgag ttcctggggg gaccatcagt cttcctgttc    60
cccccaaaac ccaaggacac tctcatgatc tcccggaccc ctgaggtcac gtgcgtggtg   120
gtggacgtga gccaggaaga ccccgaggtc cagttcaact ggtacgtgga tggcgtggag   180
gtgcataatg ccaagacaaa gccgcgggag gagcagttca acagcacgta ccgtgtggtc   240
agcgtcctca ccgtcctgca ccaggactgg ctgaacggca aggagtacaa gtgcaaggtc   300
tccaacaaag gcctcccgtc ctccatcgag aaaaccatct ccaaagccaa agggcagccc   360
```
cgagagccac aggtgtacac cctgccccca tcccaggagg agatgaccaa gaaccaggtc    420
agcctgacct gcctggtcaa aggcttctac cccagcgaca tcgccgtgga gtgggagagc    480
aatgggcagc cggagaacaa ctacaagacc acgcctcccg tgctggactc cgacggctcc    540
ttcttcctct acagcaggct aaccgtggac aagagcaggt ggcaggaggg gaatgtcttc    600
tcatgctccg tgatgcatga ggctctgcac aaccactaca cacagaagag cctctccctg    660
tctccgggta aa                                                        672

<210> SEQ ID NO 5
<211> LENGTH: 52
<212> TYPE: DNA
<213> ORGANISM: Artificial sequence
<220> FEATURE:
<221> NAME/KEY: misc_feature
<223> OTHER INFORMATION: primer

<400> SEQUENCE: 5
tttacgcgtc ctagcgctac cggtcgccac catgcagatc ccacaggcgc cc            52

<210> SEQ ID NO 6
<211> LENGTH: 40
<212> TYPE: DNA
<213> ORGANISM: Artificial sequence
<220> FEATURE:
<221> NAME/KEY: misc_feature
<223> OTHER INFORMATION: primer

<400> SEQUENCE: 6
aaaattcaaa gtctgtttca ccaccagggt ttggaactgg                          40

<210> SEQ ID NO 7
<211> LENGTH: 52
<212> TYPE: DNA
<213> ORGANISM: Artificial sequence
<220> FEATURE:
<221> NAME/KEY: misc_feature
<223> OTHER INFORMATION: primer

<400> SEQUENCE: 7
tttacgcgtc ctagcgctac cggtcgccac catgcagatc ccacaggcgc cc            52

<210> SEQ ID NO 8
<211> LENGTH: 41
<212> TYPE: DNA
<213> ORGANISM: Artificial sequence
<220> FEATURE:
<221> NAME/KEY: misc_feature
<223> OTHER INFORMATION: primer

<400> SEQUENCE: 8
ctctcggggc tgcccaccat acaccagggt ttggaactgg c                        41

<210> SEQ ID NO 9
<211> LENGTH: 27
<212> TYPE: DNA
<213> ORGANISM: Artificial sequence
<220> FEATURE:
<221> NAME/KEY: misc_feature
<223> OTHER INFORMATION: primer

<400> SEQUENCE: 9
tatggtgggc agccccgaga gccacag                                        27

```
<210> SEQ ID NO 10
<211> LENGTH: 40
<212> TYPE: DNA
<213> ORGANISM: Artificial sequence
<220> FEATURE:
<221> NAME/KEY: misc_feature
<223> OTHER INFORMATION: primer

<400> SEQUENCE: 10
aaaattcaaa gtctgtttca ctttacccgg agacagggag                          40

<210> SEQ ID NO 11
<211> LENGTH: 52
<212> TYPE: DNA
<213> ORGANISM: Artificial sequence
<220> FEATURE:
<221> NAME/KEY: misc_feature
<223> OTHER INFORMATION: primer

<400> SEQUENCE: 11
tttacgcgtc ctagcgctac cggtcgccac catgcagatc ccacaggcgc cc            52

<210> SEQ ID NO 12
<211> LENGTH: 40
<212> TYPE: DNA
<213> ORGANISM: Artificial sequence
<220> FEATURE:
<221> NAME/KEY: misc_feature
<223> OTHER INFORMATION: primer

<400> SEQUENCE: 12
aaaattcaaa gtctgtttca ctttacccgg agacagggag                          40

<210> SEQ ID NO 13
<211> LENGTH: 21
<212> TYPE: DNA
<213> ORGANISM: Artificial sequence
<220> FEATURE:
<221> NAME/KEY: misc_feature
<223> OTHER INFORMATION: primer

<400> SEQUENCE: 13
gtgaaacaga ctttgaattt t                                              21

<210> SEQ ID NO 14
<211> LENGTH: 22
<212> TYPE: DNA
<213> ORGANISM: Artificial sequence
<220> FEATURE:
<221> NAME/KEY: misc_feature
<223> OTHER INFORMATION: primer

<400> SEQUENCE: 14
ctatgttgct ccttttacgc ta                                             22

<210> SEQ ID NO 15
<211> LENGTH: 52
<212> TYPE: DNA
<213> ORGANISM: Artificial sequence
<220> FEATURE:
<221> NAME/KEY: misc_feature
<223> OTHER INFORMATION: primer

<400> SEQUENCE: 15
tttacgcgtc ctagcgctac cggtcgccac catgcagatc ccacaggcgc cc            52

<210> SEQ ID NO 16
```

```
<211> LENGTH: 22
<212> TYPE: DNA
<213> ORGANISM: Artificial sequence
<220> FEATURE:
<221> NAME/KEY: misc_feature
<223> OTHER INFORMATION: primer

<400> SEQUENCE: 16
ctatgttgct ccttttacgc ta                                            22
```

CHIMERIC ANTIGEN RECEPTOR-MODIFIED IMMUNE EFFECTOR CELL CARRYING PD-L1 BLOCKING AGENT

RELATED APPLICATIONS

This application is a national stage filing under 35 U.S.C. § 371 of international application number PCT/CN2016/103941, filed Oct. 31, 2016, which claims priority to Chinese patent application number 201510779876.5, filed Nov. 13, 2015, the entire contents of each of which are incorporated herein by reference.

TECHNICAL FIELD

The present invention belongs to the field of immunotherapy. More specifically, the present invention relates to chimeric antigen receptor-modified immune effector cells carrying a PD-L1 blocking agent.

BACKGROUND ART

Increasing attention has been paid to the role of immune effector cells (such as T lymphocytes) in the immune response of tumors. At present, T-lymphocyte-based adoptive immunotherapy has achieved a certain effect in some tumors, and this immunotherapy may overcome defects of antibody therapy, although the efficacy in most tumors is still not satisfactory. In recent years, according to the discovery that the specific recognition of target cells by CTL depends on a T lymphocyte receptor (T Cell Receptor, TCR), the scFv of an antibody against a tumor cell-associated antigen is fused with an intracellular signal activating motif such as CD3ζ or FcεRIγ of the T lymphocyte receptor, to form a chimeric antigen receptor (CAR) which is then expressed on the surface of T lymphocytes, for example by lentivirus infection or the like. These CAR T lymphocytes can selectively direct T lymphocytes to tumor cells and specifically kill the tumor in a Major Histocompatibility Complex (MHC) non-limiting manner.

The chimeric antigen receptor comprises an extracellular binding region, a transmembrane region, and an intracellular signaling region. Typically, the extracellular region contains scFv that can recognize a tumor-associated antigen, the transmembrane region utilizes the transmembrane region of molecules such as CD8, CD28 and the like, and the intracellular signaling region utilizes the intracellular signaling region of immunoreceptor tyrosine activating motif (ITAM) CD3ζ or FcεRIγ and co-stimulation signal molecules such as CD28, CD27, CD137, CD134 and the like.

The first-generation of CAR T lymphocytes comprise ITAM only as the intracellular signaling region, wherein the components of the chimeric antigen receptor are linked in the form of scFv-TM-ITAM. This kind of CAR T may stimulate the anti-tumor cytotoxic effect, but the secretion of cytokines is relatively low, and it cannot stimulate long-lasting anti-tumor effect in vivo.

The subsequently developed second-generation of CAR T lymphocytes further comprise the intracellular signaling region of CD28 or CD137 (also named as 4-1BB), wherein the components of the chimeric antigen receptors are linked in the form of scFv-TM-CD28-ITAM or scFv-TM-/CD137-ITAM. The co-stimulation of B7/CD28 or 4-1BBL/CD137 occurring in the intracellular signaling region causes the sustained proliferation of T lymphocytes, and can increase the level of secretion of cytokines such as IL-2 and IFN-γ by T lymphocytes, and meanwhile increase the surviving period in vivo and anti-tumor effects of CAR T.

The third-generation of CAR T lymphocytes developed in recent years, in which the components of the chimeric antigen receptor are linked in the form of scFv-TM-CD28-CD137-ITAM or scFv-TM-CD28-CD134-ITAM, further increase the surviving period in vivo and anti-tumor effects of CAR T.

Although immune effector cells have attractive prospects for tumor immunotherapy, their efficacy in solid tumors is still not significant, and the immune effector cells have poor survival and low activity in tumor tissues. Therefore, further research is still needed in this field in order to further improve the efficacy of immune effector cells in tumor immunotherapy.

SUMMARY OF THE INVENTION

An object of the present invention is to provide chimeric antigen receptor-modified immune effector cells carrying a PD-L1 blocking agent.

In a first aspect of the present invention, a chimeric antigen receptor-modified immune effector cell is provided, which carries or expresses a PD-L1 (programmed death ligand 1) blocking agent (Blocker).

In a preferred example, the PD-L1 blocking agent includes (but is not limited to):

soluble PD-1 (sPD-1);

a fusion peptide of soluble PD-1 and CH3 domain of hIgG4e1-Fc;

a fusion peptide of soluble PD-1 and hIgG4e1-Fc; or a specific anti-PD-L1 antibody.

In another preferred example, the soluble PD-1 includes: a signal peptide and an extracellular region; preferably, the signal peptide is encoded by a nucleotide sequence as shown in SEQ ID NO: 1; preferably, the extracellular region is encoded by a nucleotide sequence as shown in SEQ ID NO: 2.

In another preferred example, the CH3 domain of hIgG4e1-Fc is encoded by a nucleotide sequence as shown in SEQ ID NO: 2; and/or the sequence of hIgG4e1-Fc comprises a Ser to Pro mutation at position 288.

In another preferred example, the chimeric antigen receptor includes: an extracellular antigen-binding region, a transmembrane region, and an intracellular signaling region, wherein the extracellular antigen-binding region is an antibody that specifically binds to an antigen highly expressed in a tumor.

In another preferred example, the intracellular signaling region includes (but is not limited to): the sequence of the intracellular signaling region of CD3ζ, FcεRIγ, CD27, CD28, 4-1BB (CD137), CD134, CD40; or Myd88; or a combination thereof.

In another preferred example, the transmembrane region includes (but is not limited to): CD8 (e.g. CD8a) transmembrane region, CD28 transmembrane region.

In another preferred example, a hinge region is included between the extracellular antigen-binding region and the transmembrane region; preferably, said hinge region comprises: CD8 (e.g. CD8a) hinge region.

In another preferred example, the antigens highly expressed in the tumor include (but are not limited to): EGFR, GPC3, HER2, EphA2, Claudin18.1, Claudin18.2, Claudin6, GD2, EpCAM, mesothelin, CD19, CD20, ASGPR1, EGFRvIII, de4 EGFR, CD19, CD33, IL13R, LMP1, PLAC1, NY-ESO-1, MAGE4, MUC1, MUC16, LeY, CEA, CAIX, CD123.

In another preferred example, the antibody that specifically binds to the antigen highly expressed in the tumor is a single-chain antibody or a domain antibody.

In another preferred example, the immune effector cells include: T lymphocytes, NK cells or NKT cells, Treg cells.

In another aspect of the present invention, there is provided a nucleic acid construct encoding a fusion polypeptide for modifying immune effector cells, wherein the nucleic acid construct comprises a sequence encoding a PD-L1 blocking agent, a sequence encoding an extracellular antigen-binding region, a sequence encoding a transmembrane region and an intracellular signaling region, which are sequentially linked; wherein the extracellular antigen-binding region is an antibody that specifically binds to the antigen highly expressed in a tumor.

In one preferred example, the sequence encoding a PD-L1 blocking agent and the sequence encoding an extracellular antigen-binding region are linked by a sequence encoding a linker peptide; and/or a ribosomal skipping sequence (F2A) is included between the sequence encoding a PD-L1 blocking agent and the sequence encoding an extracellular antigen-binding region.

In another preferred example, the linker peptide is (Gly Gly Gly Gly Ser)$_3$.

In another aspect of the present invention, there is provided an expression vector comprising the nucleic acid construct.

In another aspect of the present invention, there is provided a virus comprising the expression vector.

In another aspect of the present invention, there is provided the use of the nucleic acid construct, or an expression vector or a virus containing the nucleic acid construct, for the preparation of chimeric antigen receptor-modified immune effector cells that target a tumor.

In one preferred example, the immune effector cells are immune effector cells that express PD-1.

In another aspect of the invention, there is provided the use of said chimeric antigen receptor-modified immune effector cells for the preparation of a tumor-inhibiting pharmaceutical composition.

In another aspect of the present invention, there is provided a pharmaceutical composition for inhibiting a tumor, comprising: the chimeric receptor-modified immune effector cells.

In another aspect of the invention, there is provided the use of a PD-L1 blocking agent for the preparation of chimeric antigen receptor-modified immune effector cells, for increasing the anti-tumor effect of the immune effector cells.

In one preferred example, the PD-L1 blocking agent comprises (but is not limited to):
soluble PD-1;
a fusion peptide of soluble PD-1 and CH3 domain of hIgG4e1-Fc;
a fusion peptide of soluble PD-1 and hIgG4e1-Fc; or a specific anti-PD-L1 antibody.

In another preferred example, the tumor is a tumor that expresses (or highly expresses) PD-L1.

In another aspect of the present invention, there is provided a method for preparing a chimeric antigen receptor-modified immune effector cell, the method comprising: introducing the nucleic acid construct into the immune effector cell.

The other aspects of the present invention will be obvious to the person skilled in the art in view of the disclosure herein.

DESCRIPTION OF FIGURES

FIG. 1. a schematic diagram of human-derived soluble PD-1 (sPD-1), sPD-1-CH3 and sPD-1-Fc fusion proteins.

FIG. 2. a schematic diagram of a fusion protein of sPD-1-Fc and M27-CAR, wherein VL and VH respectively represent a light-chain variable region and a heavy chain variable region of a single-chain antibody M27 (i.e. Y022 single-chain antibody which specifically recognizes the antigen EGFRvIII and the overexpressed EGFR, see Chinese patent application No. 201510431481.6). In the CAR region, 4-1BB-CD3 is abbreviated as BBZ, CD28-CD3 is abbreviated as 28Z, CD28-4-1BB-CD3 is abbreviated as 28BBZ.

SPECIFIC EMBODIMENTS OF THE INVENTION

Figure 3:
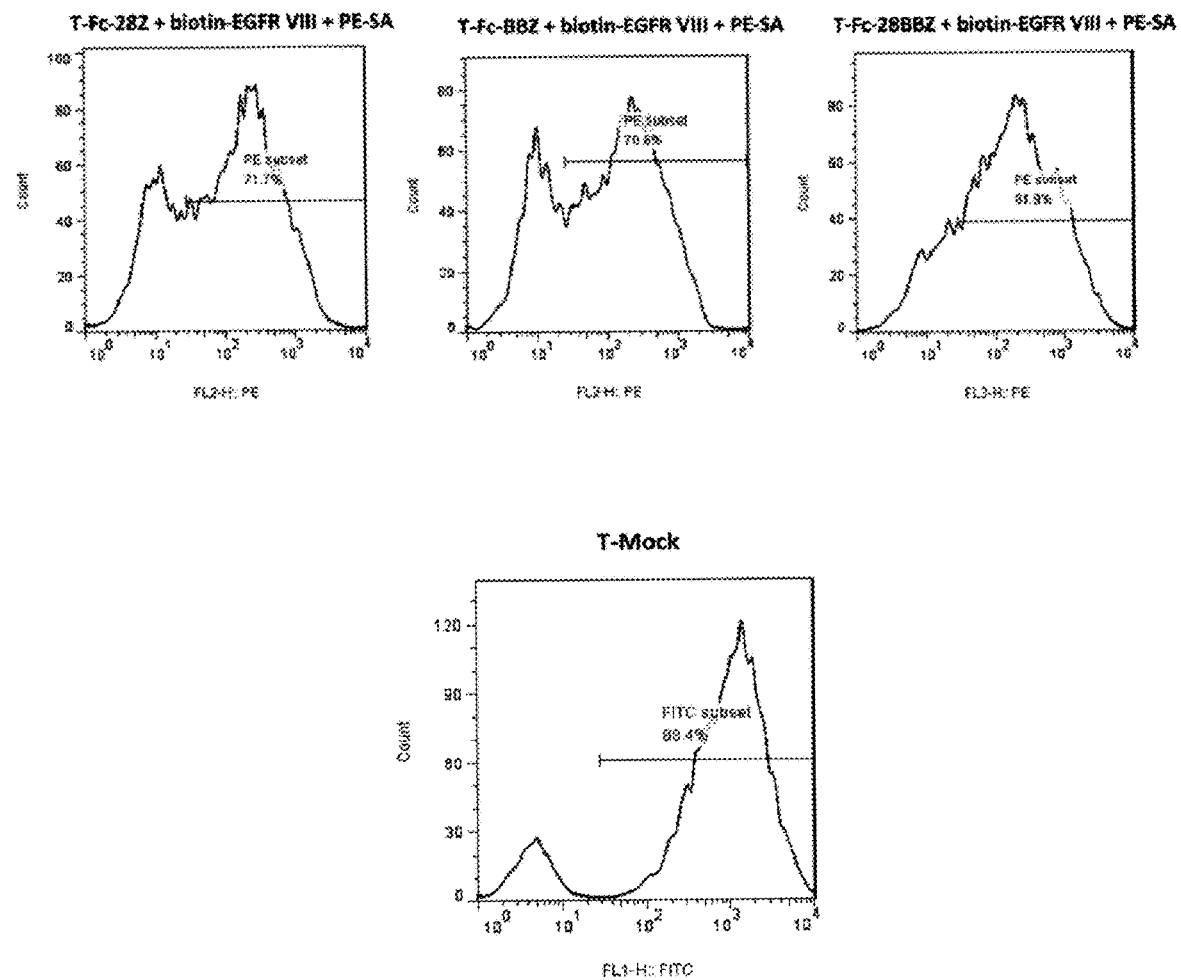
FIG. 3. Positive rate of sPD-1-CH3/sPD-1-Fc-F2A-M27 CAR T cell.

Upon intensive research, the inventors put forward a method for improving the survival and function of immune effector cells in tumors by blocking the binding of a receptor PD-1 of programmed death ligand-1 (PD-L1), expressed by the immune effector cells, to the programmed death ligand-1 expressed by tumor cells.

As used in the present invention, the "antigen highly expressed in a tumor" refers to the antigen targeted by the chimeric antigen receptor-modified immune effector cell, said antigen being highly expressed in the tumor or cells. Preferably, the "antigen highly expressed in a tumor" is a tumor-associated antigen, for example, selected from (but not limited to): EGFR, GPC3, HER2, EphA2, Claudin18.1, Claudin18.2, Claudin 6, GD2, EpCAM, mesothelin, CD19, CD20, ASGPR1, EGFRvIII, de4 EGFR, CD19, CD33, IL13R, LMP1, PLAC1, NY-ESO-1, MAGE4, MUC1, MUC16, LeY, CEA, CAIX (carbonic anhydrase IX), CD123.

In the present invention, various tumors known in the art may be included in the present invention as long as the tumors express (or highly express) the programmed death ligand-1, and express a tumor-associated antigen (an antigen highly expressed in the tumor) that is lowly expressed in normal tissues. For example, the tumors include (but are not limited to): liver cancer, lung cancer, malignant glioma, breast cancer, skin squamous cell carcinoma, oral squamous cell carcinoma, gastric cancer, prostate cancer, brain tumor, ovarian cancer, bone tumor, colon cancer, thyroid tumor, mediastinal tumor, intestinal tumor, renal tumor, adrenal tumor, bladder tumor, testicular tumor, malignant lymphoma, multiple myeloma, tumors of nervous system, esophageal cancer, pleural mesothelioma, pancreatic cancer, leukemia, head neck cancer, cervical cancer, melanoma, vaginal epithelial cancer, gallbladder cancer, malignant fibrous histiocytoma.

The term "chimeric antigen receptor-modified immune effector cells (or abbreviated as the chimeric antigen receptor immune effector cells)" is well known in the art and is an immune effector cell that is genetically engineered to express an antigen (e.g., tumor antigen)-specific chimeric receptor and capable of exerting killing effects in a targeting manner. The immune effector cells, for example, include T cells, NK cells, NKT cells, regulatory T cells (Regulatory cell, abbreviated as Treg). Conventional methods for preparing "chimeric antigen receptor-modified immune effector cells" are known to the person skilled in the art and include expressing the intracellular domains of intracellular co-stimulation signal molecules, for example, one or more of CD28 (preferably comprising CD28a, CD28b), CD137, CD27, CD3 (preferably CD3 intracellular domain), CD8, CD19, CD134, CD20, FcεRIγ. By their binding to the corresponding ligands, the second signal of the immune effector cells are activated, the proliferation ability of the immune cells and the secretion of cytokines are enhanced, and the surviving period of the immune cells is prolonged.

A very important reason for the poor survival and low activity of immune effector cells in tumor tissues may be due to solid tumor cells or other cells expressing PD-L1 and thereby affecting the survival of the chimeric antigen-modified immune effector cells (e.g., CAR T cells). Tumor cells which highly express the molecule PD-L1 bind to the receptor PD-1 on the immune effector cells, and deliver negative regulatory signals, resulting in the induced apoptosis and immune incompetence of tumor antigen-specific T cells and making the tumor cells escape from immune surveillance and killing by the body.

As an important member of co-stimulation molecules of the immunoglobulin superfamily, PD-1/PD-L1 is involved in the immunoregulatory process such as autoimmunity, transplantation immunity and tumor immunity. PD-1 is an inhibitory receptor that is mainly expressed on activated immune effector cells (such as T lymphocytes), and its binding to the ligand PD-L1 will significantly inhibit the activation and proliferation of the immune effector cells, and regulate the expression and secretion of cytokines. PD-L1 is widely expressed on a variety of immune cells, epithelial cells and tumor cells, and is overexpressed in multiple tumors. At present, many studies have shown that the PD-L1 molecule which is highly expressed in many human tumors is closely related to the clinical pathological features and prognosis of patients and becomes a new biological indicator for detection and prognosis of tumors.

Therefore, the inventors assumed that if a soluble receptor or antibody or other blocking agent of PD-L1 was secreted and expressed by the chimeric antigen-modified immune effector cells, then it would be possible that the survival and function of the chimeric antigen-modified immune effector cells in the solid tumor will be increased. Based on this assumption, the inventors have further verified that the expression of a soluble receptor of PD-L1 (sPD-1) on the immune effector cells can achieve a good antitumor activity.

As a preferred embodiment of the present invention, a schematic diagram of a structure of the chimeric antigen receptor of the present invention is shown in FIG. 1, which successively (preferably from N-terminus to C-terminus) comprises: a programmed death ligand-1 blocking agent, an extracellular antigen-binding region, a transmembrane region, and an intracellular signaling region.

The programmed death ligand-1 (PD-L1) blocking agent may be a variety of substances that can down-regulate, block, suppress and inhibit PD-L1 as long as it can prevent or competitively interfere with the interaction between PD-L1 and PD-1 which is expressed by the immune effector cells. In a preferred embodiment of the present invention, the programmed death ligand-1 blocking agent includes but is not limited to: sPD-1; a fusion peptide of sPD-1 and CH3 domain of hIgG4e1-Fc; a fusion peptide of sPD-1 and hIgG4e1-Fc; or a specific anti-PD-L1 antibody.

In a preferred embodiment of the present invention, the extracellular antigen-binding region includes an antibody that specifically recognizes an antigen highly expressed in the tumor, and is preferably a single-chain antibody. More preferably, the extracellular antigen-binding region of the chimeric antigen receptor is linked to the transmembrane region of CD8 or CD28 via the CD8 hinge region, wherein the transmembrane region is immediately followed by the intracellular signaling region.

The transmembrane region of the chimeric antigen receptor may be selected from the transmembrane region of protein CD8 or CD28 or the like. Human CD8 protein is in a heterodimeric form composed of two chains of αβ or γβ. In one embodiment of the invention, the transmembrane region is selected from the transmembrane region of CD8α or CD28. In addition, CD8α hinge region is a flexible region, and thus, the transmembrane region of CD8 or CD28 together with a hinge region are used to link the extracellular antigen-binding region to the intracellular signaling region of the chimeric antigen receptor CAR.

The intracellular signaling region may be selected from the intracellular signaling regions of proteins CD3ζ, FcεRIγ, CD28, CD137 (4-1BB), CD134, and a combination thereof. The CD3 molecule consists of five subunits, wherein the CD3ζ subunit (also known as CD3 zeta, abbreviated as Z) contains three ITAM motifs which are important signal transduction regions in the TCR-CD3 complex. CD3δZ is a truncated CD3ζ sequence having no ITAM motif and is generally constructed as a negative control in the practice of the present invention. FcεRIγ is mainly distributed on the surface of mast cells and basophils, it contains one ITAM motif and is similar to CD3ζ in terms of the structure, distribution and function. As described above, CD28, CD137, and CD134 are co-stimulation signal molecules, the co-stimulatory effects generated by their intracellular signaling segments after they bind to their respective ligands result in the sustained proliferation of the immune effector cells (mainly T lymphocytes), and can increase the level of secretion of cytokines such as IL-2 and IFN-γ by the immune effector cells and meanwhile improve the surviving period in vivo and anti-tumor effects of the CAR immune effector cells.

The chimeric antigen receptor polypeptides of the invention may be sequentially linked in the manners selected from:

extracellular antigen-binding region-CD8 transmembrane region-4-1BB-CD3ζ, extracellular antigen-binding region-CD28a-CD28b-CD3ζ, extracellular antigen-binding region-CD28a-CD28b-4-1BB-CD3ζ, and a combination thereof, wherein in the respective chimeric antigen receptor proteins, CD28a represents the transmembrane region of CD28 molecule, and CD28b represents the intracellular signaling region of CD28 molecule.

The present invention also includes a nucleic acid encoding the chimeric antigen receptor. The present invention also relates to variants of the above-described polynucleotides, which encode polypeptides having the same amino acid sequence as the present invention, or fragments, analogs and derivatives of the polypeptides.

The present invention also provides a vector containing the nucleic acid of the chimeric antigen receptor described above. The invention also comprises viruses containing the vector described above. The viruses of the present invention include the packaged infectious viruses, and also include viruses to be packaged that contain the components essential for the packaging of infectious viruses. Other viruses known in the art for introducing exogenous genes into immune effector cells and the corresponding plasmid vectors may also be used in the present invention.

The present invention also provides chimeric antigen-modified immune effector cells transfected with the nucleic acid encoding the chimeric antigen receptor or transfected with the above-mentioned recombinant plasmid containing the nucleic acid, or a virus containing the plasmid. The conventional nucleic acid transfection methods in the art including non-viral and viral transfection methods may be used in the present invention. The non-viral transfection methods include electroporation and transposon methods. The nucleic acid transfection apparatus Nucleofector recently developed by Amaxa company can directly introduce an exogenous gene into the nucleus to achieve the efficient transfection of a gene of interest. In addition, the transposon systems such as those based on the Sleeping Beauty system or the PiggyBac transposon have greater improvement on transfection efficiency than the conventional electroporation, and the combined use of the nucleofector transfection apparatus with the Sleeping Beauty transposon system has been reported [Davies J K., et al. Combining CD19 redirection and alloanergization to generate tumor-specific human T cells for allogeneic cell therapy of B-cell malignancies. Cancer Res, 2010, 70(10): OF1-10]. This method not only has high transfection efficiency but also achieves directed integration of genes of interest. In one embodiment of the invention, the method that achieves the transfection of the chimeric antigen receptor gene-modified immune effector cells is based on viruses such as retroviruses or lentiviruses. The method has advantages of high transfection efficiency, stable expression of exogenous genes, and shortening the time for the immune effector cells cultured in vitro to reach a number of clinical grade. On the surface of the transgenic immune effector cells, the introduced nucleic acid is expressed through transcription and translation. By in vitro cytotoxicity experiments on various cultured tumor cells, it was proved that the chimeric antigen-modified immune effector cells of the present invention have highly specific tumor cell killing effect (also called cytotoxicity) and can effectively survive in tumor tissues. Therefore, the nucleic acid encoding a chimeric antigen receptor, a plasmid comprising the nucleic acid, a virus comprising the plasmid, and transgenic immune effector cells transfected with the nucleic acid, plasmid or virus according to the present invention can be effectively used for immunotherapy of a tumor.

The chimeric antigen-modified immune effector cells of the present invention may further carry a sequence encoding an exogenous cytokine; the cytokine includes, but is not limited to: IL-12, IL-15 or IL-21. These cytokines have immunoregulatory or anti-tumor activity, can enhance the function of the effector T cells and the activated NK cells, or directly exert an anti-tumor effect. Therefore, the person skilled in the art can understand that the use of said cytokines helps the immune cells to function better.

The chimeric antigen-modified immune effector cells of the present invention can further express another chimeric receptor in addition to the chimeric receptor described above. This receptor does not contain CD3ζ, but contains the intracellular signaling domain of CD28, the intracellular signaling domain of CD137 or a combination of both.

The chimeric antigen-modified immune effector cells of the present invention can further express a chemokine receptors; the chemokine receptor includes but is not limited to CCR2. The person skilled in the art can understand that the CCR2 chemokine receptor and in vivo CCR2 are involved in competitive binding, which is advantageous for blocking the metastasis of tumors.

The chimeric antigen-modified immune effector cells of the present invention can further express siRNA that can decrease the PD-1 expression or a protein that can block PD-L1. The person skilled in the art can understand that competitively blocking the interaction of PD-L1 with its receptor PD-1 is advantageous for restoring the anti-tumor T cell response, thereby inhibiting tumor growth.

The chimeric antigen-modified immune effector cells of the present invention can further express a safety switch; preferably, the safety switch includes: iCaspase-9, truncated EGFR or RQR8.

The chimeric antigen receptor-modified immune effector cells of the present invention can be used for preparing a pharmaceutical composition or a diagnostic reagent. The composition may further comprise a pharmaceutically acceptable carrier in addition to an effective amount of the immune cells. The term "pharmaceutically acceptable" means that when the molecule itself and the composition are properly administered to an animal or a human, they would not produce unfavorable, allergic or other adverse reaction.

Specific examples of substances that can be used as pharmaceutically acceptable carriers or components thereof are sugars such as lactose, glucose and sucrose; starches such as corn starch and potato starch; celluloses and their derivatives such as sodium carboxymethylcellulose, ethyl cellulose and methyl cellulose; tragacanth powder; malt; gelatin; talc; solid lubricants such as stearic acid and magnesium stearate; calcium sulfate; vegetable oils such as peanut oil, cottonseed oil, sesame oil, olive oil, corn oil and cocoa oil; polyols such as propylene glycol, glycerin, sorbitol, mannitol and polyethylene glycol; alginic acid; emulsifiers such as Tween®; wetting agents such as sodium lauryl sulfate, colorants; flavoring agents; tablets, stabilizers; antioxidants; preservatives; pyrogen free water; isotonic saline solution and phosphate buffers, etc.

The composition of the present invention can be formulated into various dosage forms as required, and can be administered in a dosage that is beneficial for the patients and determined by physicians according to factors such as the species, age, weight and general disease situation of patients, administration manner and the like. The administration manner can be injection or other treatment manners.

The chimeric antigen receptor-modified immune effector cells of the invention can effectively increase the survival and function of the chimeric antigen-modified immune effector cells in tumors.

The present invention will be further described below with reference to the specific examples. It should be understood that these examples are provided only for illustrating the present invention and are not intended to limit the scope of the present invention. The experimental methods for which the specific conditions are not indicated in the following examples are generally performed according to the conventional conditions such as those described in Molecular Cloning: A Laboratory Manual, edited by J. Sambrook et al., Third Edition, Science Press, 2002, or according to the conditions recommended by the manufacturer.

Example 1. Construction of Recombinant Lentiviral Vector PRRLSIN-cPPT.EF-1α-sPD-1/sPD-1-CH3/sPD-1-Fc-F2A-M27-CAR of Soluble sPD-1-Fc Binding Chimeric Antigen (EGFR VIII) Receptor 1. The Design of Human-Derived sPD-1, sPD-1-CH3 and sPD-1-Fc Sequences (1) The Design of Human-Derived sPD-1 Sequence As shown in FIG. 1, the human-derived sPD-1 protein contains the signal peptide and the extracellular domain of PD-1. The human-derived sPD-1-CH3 protein contains the signal peptide and the extracellular domain of PD-1 and the CH3 domain of hIgG4e1-Fc linked via a linker. The human-derived sPD-1-Fc fusion protein contains the signal peptide and the extracellular domain of PD-1 as well as the hIgG4e1-Fc domain linked via a linker to increase the stability. hIgG4e1-Fc comprises a S288P mutation and thus can reduce complement-dependent cytotoxicity (CDC) and antibody-dependent cell-mediated cytotoxicity (ADCC) caused by hIgG4e1-Fc in human body. Please refer to pFUSE-hIgG4e1-Fc1 plasmid of Invivogen Company (http://www.invivogen.com/pfuse-higg4e1-fc) for the sequence of hIgG4e1-Fc.

Please make reference to Pubmed Nucleotide database for the PD-1 DNA sequence, and the corresponding serial number of PD-1 is NM_005018.2. Please make reference to Uniprot database for the signal peptide (amino acids 1-20) and the extracellular segment (amino acids 21-170) of PD-1.

The sequence of the signal peptide of PD-1:

(SEQ ID NO: 1)
ATGCAGATCCCACAGGCGCCCTGGCCAGTCGTCTGGGCGGTGCTACAACT

GGGCTGGCGG;

The sequence of the extracellular segment of PD-1:

(SEQ ID NO: 2)
CCAGGATGGTTCTTAGACTCCCCAGACAGGCCCTGGAACCCCCCCACCTT

CTCCCCAGCCCTGCTCGTGGTGACCGAAGGGGACAACGCCACCTTCACCT

GCAGCTTCTCCAACACATCGGAGAGCTTCGTGCTAAACTGGTACCGCATG

AGCCCCAGCAACCAGACGGACAAGCTGGCCGCCTTCCCCGAGGACCGCAG

CCAGCCCGGCCAGGACTGCCGCTTCCGTGTCACACAACTGCCCAACGGGC

GTGACTTCCACATGAGCGTGGTCAGGGCCCGGCGCAATGACAGCGGCACC

TACCTCTGTGGGGCCATCTCCCTGGCCCCCAAGGCGCAGATCAAAGAGAG

CCTGCGGGCAGAGCTCAGGGTGACAGAGAGAAGGGCAGAAGTGCCCACAG

CCCACCCCAGCCCCTCACCCAGGCCAGCCGGCCAGTTCCAAACCCTGGTG.

(2) The Design of Human-Derived sPD-1-CH3 Sequence sPD-1 is linked to the CH3 domain in hIgG4e1-Fc via a linker, wherein the linker sequence is TATGGT. Please make reference to the pFUSE-hIgG4e1-Fc1 plasmid for the sequence of the CH3 domain.

The DNA sequence of CH3 domain:

(SEQ ID NO: 3)
GGGCAGCCCCGAGAGCCACAGGTGTACACCCTGCCCCCATCCCAGGAGGA

GATGACCAAGAACCAGGTCAGCCTGACCTGCCTGGTCAAAGGCTTCTACC

CCAGCGACATCGCCGTGGAGTGGGAGAGCAATGGGCAGCCGGAGAACAAC

TACAAGACCACGCCTCCCGTGCTGGACTCCGACGGCTCCTTCTTCCTCTA

CAGCAGGCTAACCGTGGACAAGAGCAGGTGGCAGGAGGGGAATGTCTTCT

CATGCTCCGTGATGCATGAGGCTCTGCACAACCACTACACACAGAAGAGC

CTCTCCCTGTCTCCGGGTAAA (3) The Design of Human-Derived sPD-1-Fc Sequence sPD-1 is linked to the hIgG4e1-Fc domain via a linker, wherein the linker sequence is TATGGT. Please make reference to the pFUSE-hIgG4e1-Fc1 v01 plasmid for the sequence of the hIgG4e1-Fc domain.

The DNA sequence of hIgG4e1-Fc domain (the underlined part is a site that constitutes the S288P mutation)

(SEQ ID NO: 4)
CCCCCATGCCCACCATGCCCAGCACCTGAGTTCCTGGGGGGACCATCAGT

CTTCCTGTTCCCCCCAAAACCCAAGGACACTCTCATGATCTCCCGGACCC

CTGAGGTCACGTGCGTGGTGGTGGACGTGAGCCAGGAAGACCCCGAGGTC

CAGTTCAACTGGTACGTGGATGGCGTGGAGGTGCATAATGCCAAGACAAA

GCCGCGGGAGGAGCAGTTCAACAGCACGTACCGTGTGGTCAGCGTCCTCA

CCGTCCTGCACCAGGACTGGCTGAACGGCAAGGAGTACAAGTGCAAGGTC

TCCAACAAAGGCCTCCCGTCCTCCATCGAGAAAACCATCTCCAAAGCCAA

AGGGCAGCCCCGAGAGCCACAGGTGTACACCCTGCCCCCATCCCAGGAGG

AGATGACCAAGAACCAGGTCAGCCTGACCTGCCTGGTCAAAGGCTTCTAC

CCCAGCGACATCGCCGTGGAGTGGGAGAGCAATGGGCAGCCGGAGAACAA

CTACAAGACCACGCCTCCCGTGCTGGACTCCGACGGCTCCTTCTTCCTCT

ACAGCAGGCTAACCGTGGACAAGAGCAGGTGGCAGGAGGGGAATGTCTTC

TCATGCTCCGTGATGCATGAGGCTCTGCACAACCACTACACACAGAAGAG

CCTCTCCCTGTCTCCGGGTAAA

2. Linking sPD-1/sPD-1-CH3/sPD-1-Fc to M27-CAR sPD-1, sPD-1-CH3 or sPD-1-Fc is linked to M27-CAR, specifically by:

(1) Using the plasmid T-sPD-1-Fc containing the sPD-1-Fc sequence (purchased from Generay Biotech (Shanghai) Co., Ltd.) as a template to obtain sPD-1 sequence① from PCR amplification performed with an upstream primer 5'-ttt ACGCGTCCTAGCGCTACCGG TCGCCACCATGCA-GATCCCACAGGCGCCC-3' (SEQ ID NO: 5) and a downstream primer (SEQ ID NO: 6)
5'-AAAATTCAAAGTCTGTTTCACCACCAGGGTTTGGAACTGG-3', wherein the double underlined part is F2A overlapping sequence.

(2) Using the T-sPD-1-Fc plasmid as a template to obtain sPD-1 sequence② from PCR amplification performed with an upstream primer 5'-tttACGCGTCCTAGCGCTA CCGGTCGCCACCATGCAGATCCCACAGGCGCCC-3' (SEQ ID NO: 7) and a downstream primer (SEQ ID NO: 8)
5'-<u>CTCTCGGGGCTGCCC</u>ACCATACACCAGGGTTTGGAACTGGC-3'

(wherein purple indicates the linker, blue indicates CH3 overlapping sequence), and to obtain CH3 fragment ③ from PCR amplification performed with an upstream primer 5'-TATGGTGGGCAGCCCCGAGAGCCACAG-3' (SEQ ID NO: 9) and a downstream primer (SEQ ID NO: 10)
<u>AAAATTCAAAGTCTGTTTCAC</u>TTTACCCGGAGACAG GGAG-3', wherein the double underlined part is F2A overlapping sequence.

(3) Using T-sPD-1-Fc plasmid as a template to obtain sPD-1-Fc fragment ④ from amplification performed with an upstream primer 5'-tttACGCGTCCTAGCGC-TACCGGTCGCCACCATGCAGATCCCACAGGCGCC C-3' (SEQ TD NO: 111 and a down stream primer 5'-

(SEQ ID NO: 12)
<u>AAAATTCAAAGTCTGTTTCAC</u> TTTACCCGG AGACAGGGAG-3', wherein the double underlined part is F2A overlapping sequence.

(4) Using three kinds of plasmid pWPT-mcherry-F2A-M27-28Z/BBZ/28BBZ (purchased from Shanghai Ruijin Biotechnology Co., Ltd; the "/" in the plasmid name indicates the relationship of "or" between the preceding peptide fragments and the following peptide fragments, the same below; wherein 28Z/BBZ/28BBZ is abbreviated as CAR) respectively as a template to obtain F2A-M27-28Z/BBZ/28BBZ fragments (⑤/⑥/⑦) from PCR amplification performed with an upstream primer 5'-GTGAAACAGACTTT-GAATTT-3' (SEQ ID NO: 13) and a downstream primer 5'-CTATGTTGCTCCTTTTACGCTA-3' (SEQ ID NO: 14).

(5) Respectively splicing the fragments in equimolar amounts ①+⑤/⑥/⑦, ②+③+⑤/⑥/⑦, ④+⑤/⑥/⑦) to obtain sPD-1/sPD-1-CH3/sPD-1-Fc-F2A-M27-28Z/BBZ/28BBZ fragments from the amplification performed with an upstream primer 5'-ttt ACGCGTCCTAGCGCTACCGGTCGCCAC CATGCA-GATCCCACAGGCGCCC-3' (SEQ ID NO: 15) and a downstream primer 5'-CTATGTTGCTCCTTTTACGCTA-3' (SEQ ID NO: 16), wherein the schematic diagram of the fusion protein of sPD-1-Fc and M27-CAR is shown in FIG. 2.

PCR amplification conditions: initial denaturation: 94° C., 4 min; denaturation: 94° C., 20s; annealing: 58° C., 30s; extension: 68° C., 1000 bp/min (kod-plus); 25 cycles, and then a total extension: 68° C., 10 min.

Splicing of the nucleic acid fragments: the fragments to be spliced were added in equimolar amounts and then spliced. The splicing conditions were as follows: initial denaturation: 94° C., 4 min; denaturation: 94° C., 30s; annealing: 58° C., 30s; extension: 68° C., 1000 bp/min; 6-8 cycles, and then a total extension: 68° C., 10 min. An equal volume of PCR mixture system containing upstream and downstream primers is then added for PCR. PCR conditions were as follows: initial denaturation: 94° C., 4 min; denaturation: 94° C., 30 s; annealing: 58° C., 30 s; extension: 68° C., 1000 bp/min; 25 cycles, and then a total extension: 68° C., 10 min.

3. Construction of Recombinant Lentiviral Vector PRRLSIN-cPPT.EF-1α-sPD-1/sPD-1-CH3/sPD-1-Fc-F2A-M27-CAR The sPD-1/sPD-1-CH3/sPD-1-Fc-F2A-M27-28Z/BBZ/28BBZ fragment obtained above has a MluI restriction site at its 5' end and a SalI restriction site at its 3' end. By means of double digestion with MluI and SalI, the similarly double-digested pRRLSIN-cPPT.EF-1α vector (purchased from addgene, see Chinese Patent Application No. 201510481235.1) was ligated to construct a lentiviral vector which can successfully express sPD-1/sPD-1-CH3/sPD-1-Fc protein and each chimeric antigen receptor.

In summary, M27-CAR targeting EGFR$^{287-302}$ was respectively ligated with sPD-1/sPD-1-CH3/sPD-1-Fc by ribosome skipping sequence F2A to obtain a bicistronic gene. By means of restriction sites MluI and SalI, the fragment containing the dicistronic gene of interest was ligated into pRRLSIN-cPPT.EF-1α vector digested with MluI and SalI to successfully construct a recombinant expression vector of interest. The constructed recombinant lentiviral vectors were identified by sequencing. After the vectors were determined to be correctly constructed, the lentiviral packaging was performed.

Example 2. Preparation of Lentivirus and Expression of Chimeric Antigen Receptor on T Lymphocytes 1. Preparation, Concentration and Titration of Lentivirus 1) 293T cells which were cultured to $6^{th}$ to $10^{th}$ generation were plated at a density of $1.2 \times 10^7$ in DMEM medium supplemented with 10% fetal bovine serum (Gibco) in a 15 cm culture dish, and cultured overnight at 37° C., 5% $CO_2$ to prepare for transfection.

2) 10.8 μg of the target gene plasmid PRRLSIN-cPPT.EF-1α-EGFP(Mock) or PRRLSIN-cPPT.EF-1α-sPD-1/sPD-1-CH3/sPD-1-Fc-F2A-M27-CAR was dissolved in 800 μL blank DMEM medium respectively with 12.4 μg of the packaging plasmid pRsv-REV, 12.4 μg of the packaging plasmid RRE-PMDLg, 4.8 μg of the packaging plasmid Vsvg, and mixed to achieve homogeneity.

3) 60 μg PEI (1 μg/μl) was dissolved in 800 μl serum-free DMEM medium, mixed gently (or vortexed for 5 seconds at 1000 rpm), and incubated for 5 min at room temperature.

4) A transfection complex was formed by adding the plasmid mixture to the PEI mixture, immediately followed by vortex or gentle mixing and then incubation for 20 min at room temperature.

5) 1.6 ml of the transfection complex was added dropwisely to a 10 cm culture dish containing 11 ml of DMEM medium (no need to replace the medium).

6) After 4-5 hours, the medium was replaced with DMEM medium supplemented with 10% FBS for the transfected 293T cells.

7) Incubation at 37° C. for 72h and collecting virus supernatant.

8) 5×PEG8000 NaCl was formulated by weighing and dissolving 8.766 g of NaCl and 50 g of PEG8000 in 200 ml of Milli-Q pure water, followed by moist heat sterilization at 121° C. for 30 min, and was stored at 4° C.

9) The lentivirus supernatant was filtered using a 0.45 μm filter; 10) 7.5 ml of 5×PEG-8000 NaCl stock solution was added to each 30 ml of the initial filtered virus solution;

11) Mix every 20-30 min, for a total of 3 to 5 times;

12) Stand overnight at 4° C.;

13) Centrifuge at 4000 g, 4° C. for 20 min;

14) Discard the supernatant, allow the tube to stand for 1-2 minutes, and remove the residual liquid;

15) An appropriate amount of a solution for dissolving the lentivirus was added to dissolve the lentivirus pellet;

16) The collected virus suspension was aliquoted into 200 μl each, preserved in the finished tube, and stored at −80° C.;

17) The titer of the lentivirus packaged with a recombinant vector was determined by infecting 293T cells using the limiting dilution:

18) 293T cells were plated in a 6-well plate at a number of $2\times10^5$ cells, 1 ml/well; to which polybrene solution at an initial concentration of 10 μg/μl was added at 0.6 μl/ml to achieve the final concentration of 6 μg/ml; and cultured at 37° C., 5% $CO_2$ for 1 hour, wherein the culture medium is DMEM sulpemented with 10% fetal bovine serum;

19) The virus concentrate 5× diluted, 3 gradients, was added at 10 μL/well, and cultured at 37° C., 5% $CO_2$ 20) At 72 hours after infection, 293T cells were trypsinized (30s), and added with 1 ml of DMEM (10% FBS) to stop digestion; the cell suspension was transferred to a 2 ml centrifuge tube (two aliquots), centrifuged at 5000 rpm for 5 min to discard the supernatant; washed twice with PBS;

21) One group was added with PE-SA (control). PE-SA was diluted at 1:50, 50 μl of the diluted PE-SA was added to each of the centrifuge tubes, dispersed by pipetting, and incubated on ice for 45 min; washed twice with PBS (1% NBS), added with 400 μl PBS (1% NBS), and transferred to a flow tube; wherein the full name of PE-SA is ethidium bromide labeled streptomycin, for binding to a biotin-labeled recombinant EGFR-VIII protein.

22) The other group was added with EGFRvIII-biotin (25 μg/ml). 50 μl EGFRvIII-biotin (25 μg/ml, purchased from Shanghai Ruijin Biotechnology Co., Ltd.) was added to each tube, incubated on ice for 45 min, washed twice with PBS (1% NBS), added with 1:50 diluted PE-SA solution, incubated on ice for 45 min; washed twice with PBS (1% NBS), added with 400 μl PBS (1% NBS), and transferred to a flow tube. Flow cytometry was used to detect the PE channel, cell number with a positive rate of 5~20% was appropriate, the titer was calculated according to the equation: titer (U/mL) =the number of cells×the positive rate/virus volume. EGFRvIII-biotin indicates biotinylated recombinant EGFRvIII proteins, for binding to M27 scFV on the surface of T cells after infection with the chimeric antigen receptor lentivirus.

2. Preparation of T Lymphocytes Transfected with Lentivirus—CAR positive T lymphocytes 1) T lymphocytes activation: lymphocytes were added to a culture medium at a density of about $1\times10^6$/mL, magnetic beads (Invitrogen) coated with anti-CD3 and -CD28 antibodies both were added at a ratio of magnetic beads: cells of 1:1 and a recombinant human IL-2 (Shanghai Huaxin Biotechnology Co., Ltd) was also added at a final concentration of 300 U/mL, stimulating culture for 48 hours;

2) Retronectin was used to coat a 24-well plate by adding 380 μl 5 μg/ml of Retronectin solution (PBS) to each well, followed by incubation overnight at 4° C.; 3) Remove the Retronectin solution (PBS) in the 24-well plate, wash twice with 1 ml PBS;

4) At 1 hour before infection, polybrene was added at a final concentration of 10 μg/mL to increase the infection efficiency, the cells were plated into the 24-well plate coated with Retronectin, at a cell number of $3\times10^5$/well in a medium volume of 600 μl;

5) The concentrated lentiviruses were added to PBMCs at MOI=10, centrifuged at 32° C., 1800 rpm for 40 min, and transferred to the cell incubator;

6) Proliferation: the infected cells were passaged every other day at a density of $5\times10^5$/mL and at the same time, recombinant human IL-2 was added to the lymphocyte culture medium at a final concentration of 300 U/mL.

3. Expression of Chimeric Antigen Receptor on T Lymphocyte

Human T lymphocytes were stimulated with αCD3/αCD28 magnetic beads for 48 h, and then infected with a high titer of lentivirus at MOI=10. On the 7th day after infection, the positive rate of T lymphocytes infected with lentivirus was detected by EGFRvIII-biotin+PE-SA flow assay.

1) On the $7^{th}$ day of culture, $1\times10^6$T lymphocytes infected with lentivirus were aliquoted into two 2 ml centrifuge tubes;

2) Centrifuge for 5 min at 4° C., 5000 rpm, discard the supernatant and wash twice with PBS 3) One group was added with PE-SA (control). PE-SA was diluted at 1:50, 50 μl of the diluted PE-SA was added to each of the centrifuge tubes, dispersed by pipetting, and incubated on ice for 45 min; washed twice with PBS (1% NBS), added with 400 μl PBS (1% NBS), and transferred to a flow tube;

4) The other group was added with EGFRvIII-biotin (25 μg/ml). 50 μl EGFRvIII-biotin (25 μg/ml) was added to each tube, incubated on ice for 45 min, washed twice with PBS (1% NBS), added with 1:50 diluted PE-SA solution, incubated on ice for 45 min, washed twice with PBS (1% NBS), added with 400 μl PBS (1% NBS), and transferred to a flow tube. Flow cytometry was used to detect the PE (FL2) channel.

5) The positive rate of CAR positive T cells transfected with different chimeric antigen receptors was determined by the software FlowJo.

The result of the positive rate of sPD-1-CH3/sPD-1-Fc-F2A-M27 CAR T cells was shown in FIG. 3. The positive rate of CAR T (T-CH3-28Z) cell that expresses sPD-1-CH3-M27-28Z was 66.8%, sPD-1-CH3-M27-BBZ (T-CH3-BBZ) was 66.3%, sPD-1-CH3-M27-28BBZ (T-CH3-28BBZ) was 64.1%, sPD-1-Fc-M27-28Z (T-Fc-28Z) was 71.7%, sPD-1-Fc-M27-BBZ (T-Fc-BBZ) was 70.6%, sPD-1-Fc-M27-28BBZ was 81.9%, and the positive rate of T cells (T-Mock) expressing the control Mock was 88.4%.

4. Expression of sPD-1-CH3/sPD-1-Fc in the Infected T Cells & Supernatant

The cells and supernatant were collected from the above lentivirus-infected T cells. The proteins in the supernatant were immunoprecipitated with protein A/G. The expression of sPD-1-CH3/sPD-1-Fc in the supernatant of the infected T cells was detected by Western blotting after protein denaturation.

Figure 4:
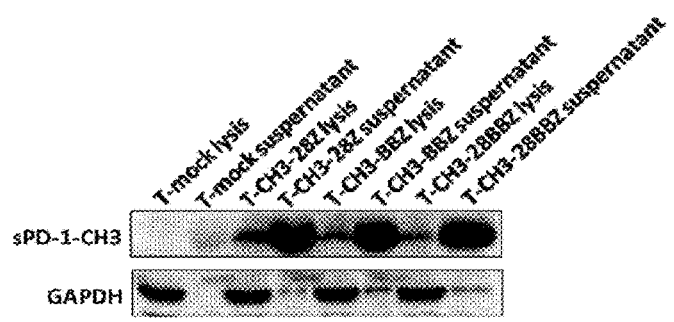
FIG. 4. Expression of sPD-1-CH3/sPD-1-Fc in the infected T cell & supernatant, wherein the lysis represents a lysate and the supernatant represents a supernatant.
Figure 4:
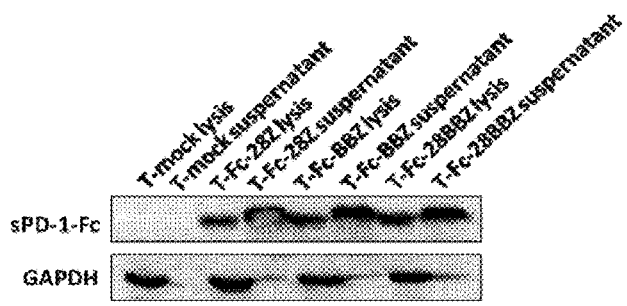

The result of the expression of sPD-1-CH3/sPD-1-Fc in the infected T cells & supernatant was shown in FIG. 4. sPD-1-CH3/sPD-1-Fc can be detected both in the supernatant of the infected T cells and in the cells.

Example 3. Exposure of $EGFR^{287-302}$ Antigen Epitope on Tumor Cell Lines

Flow assay was used to detect the exposure of the tumor-specific epitope $EGFR^{287-302}$ in U87, U87-EGFR, U87-EGFRvIII, CAL27, A431, and MDA-MB-468 cell lines. The CH12 antibody (see Chinese patent No. ZL200810038848.8) used in the flow assay can be specifically against the $EGFR^{287-302}$ epitope.

1) The following tumor cells were cultured in 6 cm dishes: U87, U87-EGFR, U87-EGFRvIII, A431, CAL27, and MDA-MB-468;

2) The cells were treated with 10 mM EDTA, dispersed by pipetting in 2M1 EP tubes, centrifuged at 3000~4000 rpm for 5 min. The cells were resuspended in 1% NPBS, aliquoted at 2×10⁶/tube, as control and test sample, 2 mL 1% NPBS, centrifuged at 3000~4000 rpm for 5 min;

3) 20 μg/mL CH12 antibody was added as the primary antibody, the control antibody of the same isotype is normal human IgG1 antibody, 20 μg/mL 100 μL/sample; vortexed fully (45s), ice bath for 45 min;

4) Remove the free primary antibody: 2 mL 1% NPBS, centrifuge at 3000~4000 rpm for 5 min, vortex fully and repeat once;

5) Add the secondary antibody: goat anti-human IgG-FITC:1:50, 100 μL/EP, ice bath for 45 min;

6) Remove the free secondary antibody: 1% NPBS, centrifuge at 3000-4000 rpm for 5 min, vortex fully and repeat once;

7) 200~500 μL 1% NPBS was added to resuspend the cells which were then transferred to a flow tube for detection.

Figure 5:
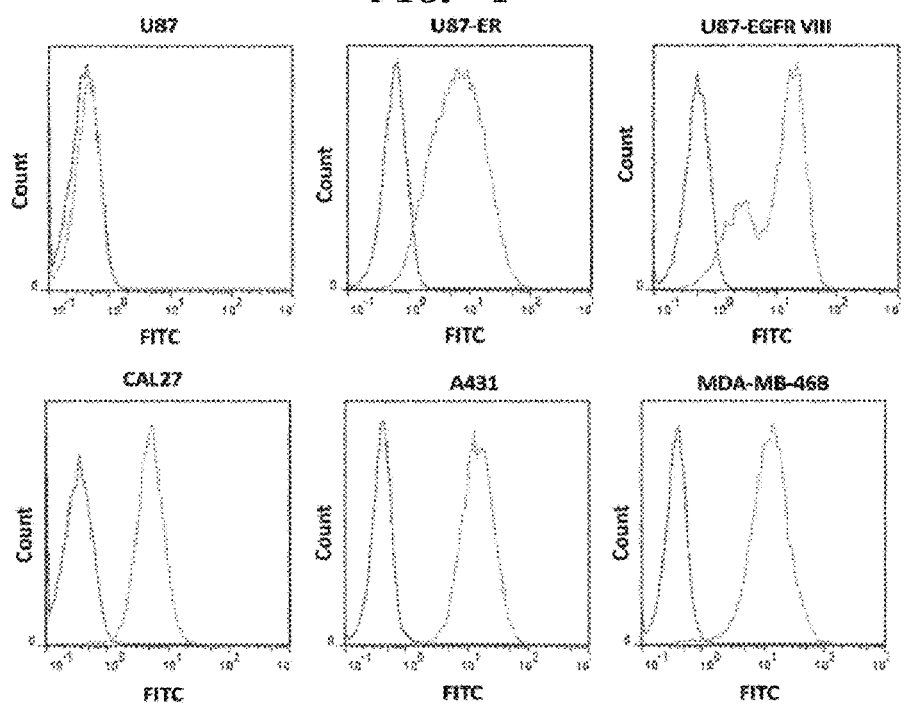
FIG. 5. Exposure of EGFR$^{287-302}$ epitope in tumor cell lines.

The results of flow assay were shown in FIG. 5. It can be seen from the results that U87 cells express EGFR at a normal level, and the CH12 antibody does not bind to the cells; and when EGFR and EGFR-VIII are overexpressed, CH12 can bind to the cells. In FIG. 5, CAL27, A431, and MDA-MB-468 are tumor cells that highly express EGFR, and the exposure of EGFR$^{287302}$ epitope can also be detected on the cell surface.

Example 4. Expression Level of PD-L1 in Tumor Cell Lines

Malignant glioma cells U87, U87-EGFR, U87-EGFRvIII, skin squamous cell carcinoma A431, oral squamous cell carcinoma cell CAL27, breast cancer cell MDA-MB-468, human immortalized epidermal cell HACAT were plated in 60 cm culture dishes. A cell lysis solution was used to lyse the cells to extract total cellular protein. The expression of PD-L1 in each tumor cell line was detected by Western blotting.

Figure 6:
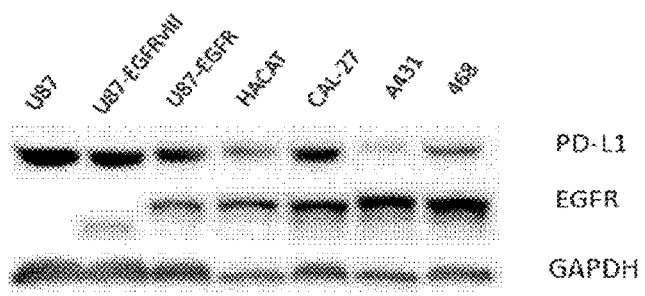
FIG. 6. Analysis of expression of PD-L1 and EGFR in various tumor cell lines.

The test results are shown in FIG. 6, indicating that PD-L1 is expressed in various tumors.

Example 5. In Vitro Toxicity Test

The in vitro killing effect of T lymphocytes which express sPD-1-CH3/Fc-F2A-M27-28Z, sPD-1-CH3/Fc-F2A-M27-BBZ, sPD-1-CH3/Fc-F2A-M27-28BBZ and were infected with the blank vector Mock was detected on U87-EGFR, U87-EGFRvIII, A431, and CAL27 at effector/target ratios of 3:1, 1:1, 1:3, respectively, wherein the cells were co-cultured for 18h. Details are given below:

1) Target cells: 50 μL 2×10⁵/mL of U87, U87-EGFR, U87-EGFRvIII, A431, CAL27, MDA-MB-468 were respectively plated into 96-well plates;

2) Effector cells: T-Mock, M27-CAR T cells (M27-28Z CAR T cells, M27-BBZ CAR T cells or M27-28BBZ CAR T cells, respectively), sPD-1-CH3/Fc-F2A-M27 CAR T cells (sPD-1-CH3/Fc-F2A-M27-28Z CAR T cells, sPD-1-CH3/Fc-F2A-M27-BBZ CAR T cells or sPD-1-CH3/Fc-F2A-M27-28BBZ CAR T cells, respectively) were added at an effector/target ratio of 3:1, 1:1 or 1:3;

3) Each group was set in quadruplicate and an average value was taken from the replicates of 4 wells. The detection time point is at 18 h.

Experimental groups and control groups are as follows:

Respective experimental group: respective target cells +CTL expressing a different chimeric antigen receptor;

Control group 1: target cells which release a maximum of LDH;

Control group 2: target cells which spontaneously release LDH;

Control group 3: effector cells which spontaneously release LDH;

4) Detection method: CytoTox 96 non-radioactive cytotoxicity detection kit (Promega Company) was adopted. This method is based on a colorimetric detection method and can replace the $^{51}$Cr release method. The CytoTox 96® assay was used to quantitatively determine lactate dehydrogenase (LDH). LDH is a stable cytosolic enzyme that is released when cells are lysed, and the release manner thereof is substantially the same as the release manner of $^{51}$Cr in radioactivity analysis. The released LDH in the medium supernatant can be detected by an enzymatic reaction of 30-minute coupling, in which LDH converts a tetrazolium salt (INT) into red Formazan. The amount of the generated red product is in direct proportion to the number of lysed cells. Please see instructions of the CytoTox 96 non-radioactive cytotoxicity detection kit for details.

5) The cytotoxicity is calculated according to the following equation:

$$\text{Cytotoxicity \%} = \frac{\text{Experimental group} - \text{control group 2} - \text{control group 3}}{\text{Control group 1} - \text{control group 2}} \times 100\%;$$

Figure 7:
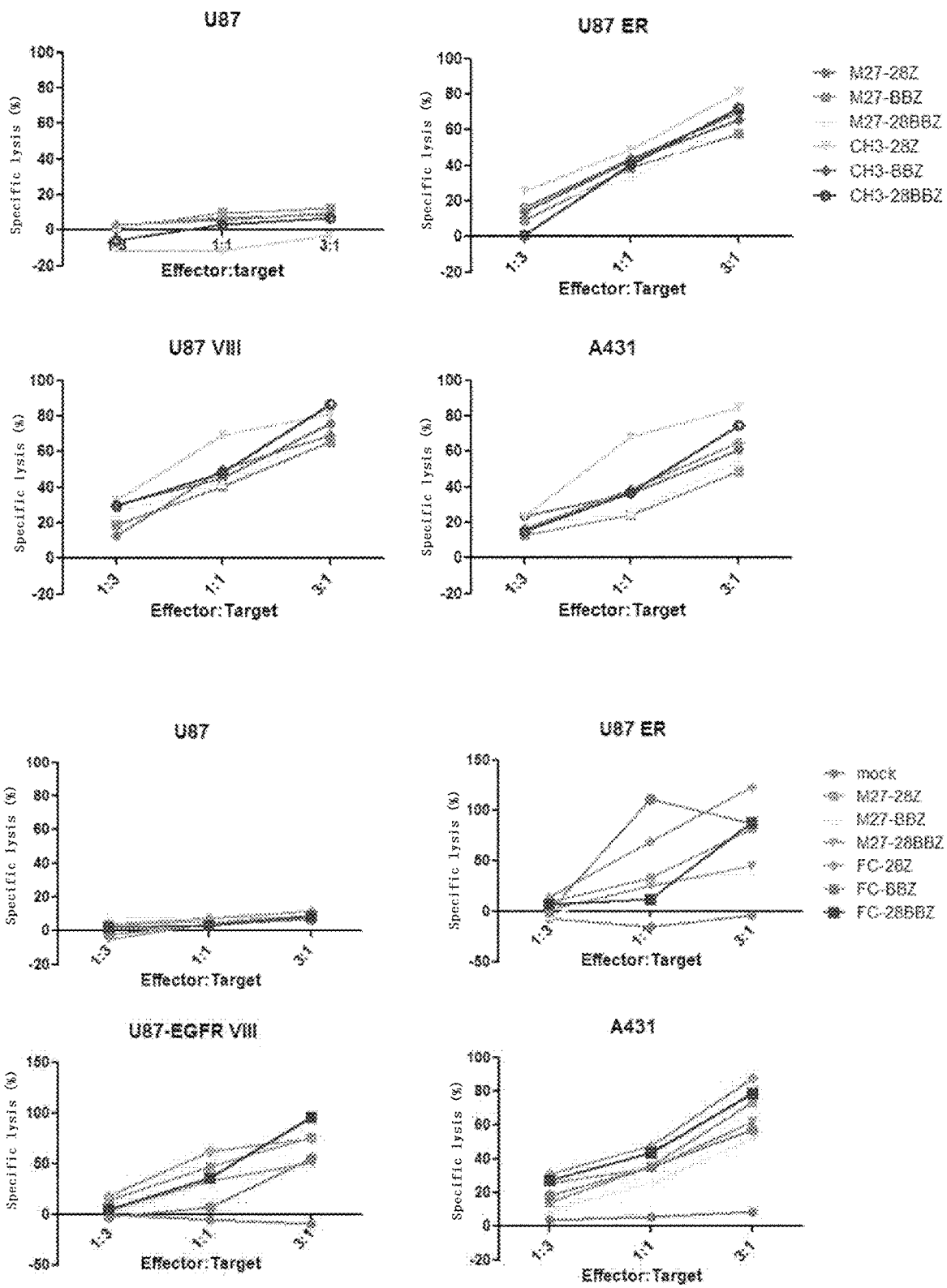
FIG. 7. The killing effect of sPD-1-Fc-F2A-M27 CAR T cells on U87-EGFR, U87-EGFRvIII, A431, and CAL27. In this figure, M27-28Z, M27-BBZ, and M27-28BBZ indicate results of experiments in which T lymphocytes expressing M27-28Z, M27-BBZ, or M27-28BBZ only were introduced; FC-28Z, FC-BBZ, FC-28BBZ indicate results of experiments in which T lymphocytes expressing sPD-1-Fc-F2A-M27-28Z, sPD-1-Fc-F2A-M27-BBZ, sPD-1-Fc-F2A-M27-28BBZ were introduced.

The killing effect of sPD-1-Fc-F2A-M27 CAR T cells on U87-EGFR, U87-EGFRvIII, A431, and CAL27 is shown in FIG. 7. The results showed that the killing effect of M27-28Z T cells expressing CH3 on U87-VIII, U87-ER and A431 cells was significantly better than that of M27-28Z T cells; the killing effect of M27-28Z/BBZ T cells expressing sPD-1-Fc on U87-ER cells was significantly better than that of M27-28Z/BBZ T cells that did not express sPD-1-Fc.

All the references mentioned in this application are incorporated herein by reference, as if each was individually incorporated herein by reference. In addition, it should be understood that with the above teachings of the present invention, the person skilled in the art can make various changes or modifications to the present invention, and these equivalent forms also fall within the scope defined by the appended claims of the present application.

The invention claimed is:

1. An immune effector cell modified to express:
   (i) a chimeric antigen receptor (CAR); and
   (ii) a PD-L1 blocking agent that is chosen from:
      (a) a soluble PD-1;
      (b) a fusion peptide of soluble PD-1 and CH3 domain of hIgG4e1-Fc; or
      (c) a fusion peptide of soluble PD-1 and hIgG4e1-Fc,
   wherein the PD-L1 blocking agent is not a component of the CAR, and
   wherein the soluble PD-1 comprises a signal peptide and an extracellular region of PD-1 but does not comprise a transmembrane domain of PD-1.

2. The immune effector cell according to claim 1, wherein the signal peptide is encoded by the nucleic acid sequence set forth in SEQ ID NO: 1.

3. The immune effector cell according to claim 1, wherein the CH3 domain of hIgG4e1-Fc is encoded by the nucleotide sequence as shown in SEQ ID NO: 3; and/or the sequence of hIgG4e1-Fc comprises a Ser to Pro mutation at position 288.

4. The immune effector cell according to claim 1, wherein the CAR comprises an extracellular antigen-binding region, a transmembrane region, and intracellular signaling region, wherein the extracellular antigen-binding region is an antibody that specifically binds to an antigen highly expressed in a tumor.

5. The immune effector cell according to claim 4, wherein the intracellular signaling region is the sequence of the intracellular signaling region of CD3ζ, FcεRIγ, CD27, CD28, 4-1BB, CD134, CD40; or Myd88; or a combination thereof.

6. The immune effector cell according to claim 4, wherein the transmembrane region is a CD8 transmembrane region, or a CD28 transmembrane region.

7. The immune effector cell according to claim 4, wherein the antigen highly expressed in the tumor is: EGFR, GPC3, HER2, EphA2, Claudin18.1, Claudin18.2, Claudin6, GD2, EpCAM, mesothelin, CD19, CD20, ASGPR1, EGFRvIII, de4 EGFR, CD19, CD33, IL13R, LMP1, PLAC1, NY-ESO-1, MAGE4, MUC1, MUC16, LeY, CEA, CAIX, or CD123.

8. The immune effector cell according to claim 1, wherein the immune effector cell comprises a T lymphocyte, NK cell, NKT cell, or Treg cell.

9. A pharmaceutical composition comprising the immune effector cell of claim 1.

10. The immune effector cell according to claim 1, wherein the extracellular region of PD-1 is encoded by the nucleotide sequence as shown in SEQ ID NO: 2.

11. The immune effector cell according to claim 4, wherein the tumor is a tumor expressing PD-L1.

* * * * *